(12) United States Patent
Cantor et al.

(10) Patent No.: US 6,743,590 B1
(45) Date of Patent: *Jun. 1, 2004

(54) METHODS FOR DIFFERENTIATING AND MONITORING PARATHYROID AND BONE STATUS RELATED DISEASES

(75) Inventors: Thomas L. Cantor, El Cajon, CA (US); Ping Gao, San Diego, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/344,639

(22) Filed: Jun. 26, 1999

Related U.S. Application Data

(63) Continuation-in-part of application No. 09/231,422, filed on Jan. 14, 1999, now Pat. No. 6,689,566.

(51) Int. Cl.[7] .................. G01N 33/53; G01N 33/537; G01N 33/536; C07K 16/00
(52) U.S. Cl. .................. 435/7.1; 435/7.94; 436/518; 436/536; 436/811; 530/388.24; 530/389.2
(58) Field of Search .................. 435/7.94, 7.1; 436/87, 518, 536, 548, 811; 530/388.24, 389.2

(56) References Cited

U.S. PATENT DOCUMENTS

| | | | |
|---|---|---|---|
| 4,369,138 A | 1/1983 | Lindall | 260/112.5 |
| 4,423,037 A | 12/1983 | Rosenblatt et al. | 424/177 |
| 4,508,828 A | 4/1985 | Lindall et al. | 436/500 |
| 4,656,250 A | 4/1987 | Morita et al. | 530/324 |
| 6,030,790 A | 2/2000 | Adermann et al. | 435/7.1 |

FOREIGN PATENT DOCUMENTS

| | | |
|---|---|---|
| DE | 33 47 548 | 7/1985 |
| DE | 44 34 551 | 4/1996 |
| EP | 0 783 522 | 12/2001 |
| WO | WO 91/06564 | 5/1991 |
| WO | WO 93/06845 | 4/1993 |
| WO | WO 94/03201 | 2/1994 |
| WO | WO 96/10041 | 4/1996 |

OTHER PUBLICATIONS

Brossard et al., 1996. Accumulation of a non–(1–84) molecular form of parathyroid hormone (PTH) detected by intact PTH assay in renal failure: importance in the interpretation of PTH values. Journal of Clinical Endocrinology and Metabolism 81: 3923–3929.*

Lepage et al., 1998. A non–(1–84) circulating parathyroid hormone (PTH) fragment interferes significantly with intact PTH commercial assay measurements in uremic samples. Clinical Chemistry 44:805–809.*

Campbell, 1991. *Monoclonal Antibody and Immunosensor Technology*, Elsevier, Amsterdam. Pp. 3–6 and 45.*

(List continued on next page.)

*Primary Examiner*—Long V. Le
*Assistant Examiner*—Changhwa J. Cheu
(74) *Attorney, Agent, or Firm*—Morrison & Foerster LLP

(57) ABSTRACT

The present invention relates to novel methods and devices for differentiating in a patient parathyroid diseases, such as hyperparathyroidism and related bone diseases, from normal or non-disease states. One detects whole or non-fragmented (1 to 84) parathyroid hormone in a biological sample and also a large non-whole parathyroid hormone peptide fragment that can function as a parathyroid hormone antagonist. By either comparing values or using independently the value of either the large non-whole parathyroid hormone peptide fragment, the whole parathyroid hormone, or the combination of these values one is able to differentiate parathyroid and bone related disease states, as well as differentiate such states from normal states.

27 Claims, 12 Drawing Sheets

OTHER PUBLICATIONS

Gao et al., 1996. Immunochemiluminometric assay with two monoclonal antibodies against the N-terminal sequence of human parathyroid hormone. Clinica Chimica Acta 245: 39–59.*

John et al., Nov. 1999. Journal of Clinical Endocrinology and Metabolism 84: 4287–4290.*

Adermann, et al., in: Innovations and Perspectives in Solid Phase Synthesis, Epton (ed.), Mayflower World Wide, Birmingham (1994) pp. 429–432.

Atkinson et al., Journal of Immunoassay (1982) 3(1):31–51.

Blind et al., Clin. Chem. (1987) 33(8):1376–1381.

Bowie et al., Science (1990) 247:1306–1310.

Brossard et al., Journal of Clinical Endocrinology and Metabolism (1996) 81(11):3923–3929.

Campbell, Monoclonal Antibody and Immunosensor Technology, in Laboratory Techniques in Biochemistry and Molecular Biology, van der Vliet (ed.), Elsevier (1991) pp. 1–11, 42–45.

Caporale and Rosenblatt, Paraththyroid Hormone Antagonists Effective in vivo, in: Advances in Experimental Medicine and Biology, New York (1986) pp. 315–327.

Clinical Chemistry (1999) 45(6)Suppl:A97 b, Abstract Nos. 339–341.

D'Amour et al., Am. J. Physiol. (1986) 251:E680–E687.

Daniel et al., Virology (1994) 202:540–549.

Fischer et al., The Journal of Clinical Investigation (1974) 54:1382–1394.

Gao et al., Clinica Chimica Acta (1996) 245:39–59.

Gordon et al., Parathyroid Hormone Domain for Protein Kinase C Stimulation Located within Amphiphilic Helix, in: Peptides: Chemistry and Biology, Proceedings of the Twelfth American Peptide Symposium, Jun. 16–21, 1991, Cambridge, MA, Smith and Rivier (eds.) Escom Science Publishers (1992) pp. 37–39.

Hashimoto et al., Journal of Cardiovascular Pharmacology (1981) 3(4):668–676.

Hehrmann et al., Journal of Immunoassay (1980) 1(2):151–174.

John et al., Journal of Clinical Endocrinology and Metabolism (1999) 84(11):4287–4290.

LePage et al., Clin. Chem. (1998) 44:805–810.

Logue et al., Journal of Immunological Methods (1991) 137:159–166.

Mägerlein et al., Arzneim.–Frosch./Drug Res. (1998) 48(1):197–204.

Mägerlein et al., Arzneim.–Forsch./Drug Res. (1998) 48(II):783–787.

Mallette, Journal of Clinical Endocrinology and Metabolism (1980) 50(1):201–203.

Nakamura et al., Endocrinol. JPN (1981) 28(4):547–549.

Ngo et al., The Protein Folding Problem and Tertiary Structure Prediction, Merz et al., (eds.), Birkhäuser boston (1994) pp. 492–495.

Niall et al., Proc. Natl. Acad. Sci. USA (1974) 71(2):384–388.

Nussbaum et al., Chemical Abstracts (1982) 96(5):181–192.

Pang et al., Pharmacol. Exp. Ther. (1981) 216(3):567–571.

Qi et al., Am. J. Kidney Dis. (1995) 26:622–631.

Quarles et al., J. Clin. Endocrinol. Metab. (1992) 75:145–150.

Stadler, Homologous Radioimmunoassay for Human Parathyroid Hormone (Residues 1–34) with Biotinylated Peptide as Tracer, in Calcium Regulating Hormones, Vitamin D Metabolites, and Cyclic AMP Assays and their Clinical Application, Schmidt–Gayk et al., (eds.), Berlin/Heidelberg, Springer, (1990) pp. 137–150.

Tampe et al., J. Immunoassay (1992) 13(1):1–13.

Visser et al., Acta Endocrinology (1979) 90:90–102.

Wingender et al., Structure–Function Relationship in Parathyroid Hormone in: Advances in Protein Design, International Workshop, Blöcker et al. (eds.), VCH (1988) pp. 167–176.

Zanelli et al., Journal of Immunoassay (1983) 4(2):175–206.

* cited by examiner

Whole Human PTH (1-84)

Standard Curve for Whole PTH Assay

Whole PTH

Big PTH 7-84 Fragment

METHODS FOR DIFFERENTIATING AND MONITORING PARATHYROID AND BONE STATUS RELATED DISEASES

RELATED APPLICATIONS

The present application is a continuation-in-part of a non-provisional utility patent application filed in the United States Patent and Trademark Office, Ser. No. 09/231,422, filed Jan. 14, 1999, now U.S. Pat. No. 6,689,566.

TECHNICAL FIELD

The present invention relates to novel methods and devices for differentiating in a patient parathyroid diseases, such as hyperparathyroidism, from normal or non-disease states. One detects whole or non-fragmented (1 to 84) parathyroid hormone in a biological sample and also a large non-whole parathyroid hormone peptide fragment that can function as a parathyroid hormone antagonist. By either comparing values or using independently the value of either the large non-whole parathyroid hormone peptide fragment, the whole parathyroid hormone, or the combination of these values one can differentiate parathyroid and bone related disease states, as well as differentiate such states from normal states.

BACKGROUND ART

Calcium plays an indispensable role in cell permeability, the formation of bones and teeth, blood coagulation, transmission of nerve impulse, and normal muscle contraction. The concentration of calcium ions in the blood is, along with calcitrol and calcitonin, regulated mainly by parathyroid hormone (PTH). Although calcium intake and excretion may vary, PTH serves through a feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

The complete form of human PTH, sometimes referred to in the art as hPTH but referred to in the present invention either as whole PTH or wPTH, is a unique 84 amino acid peptide (SEQ ID NO. 1), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism. For example, whole PTH can be cleaved between amino acids 34 and 35 to produce a (1–34) PTH N-terminal fragment and a (35–84) PTH C-terminal fragment. Likewise, clipping can occur between either amino acids 36 and 37 or 37 and 38. Recently, a large PTH fragment referred to as "non-(1–84) PTH" has been disclosed which is clipped closer to the N-terminal end of PTH. (See R. LePage et alia, "*A non-(1–84) circulating parathyroid hormone* (PTH) *fragment interferes significantly with intact PTH commercial assay measurements in uremic samples*" Clin Chem (1998); 44: 805–810.)

The clinical need for accurate measurement of PTH is well demonstrated. Serum PTH level is one of the most important indices for patients with the following diseases: familial hypocalciuria; hypercalcemia; multiple endocrine neoplasia types I and II; osteoporosis; Paget's bone disease; primary hyperparathyroidism—caused by primary hyperplasia or adenoma of the parathyroid glands; pseudohypoparathyroidism; and renal failure, which can cause secondary hyperparathyroidism.

PTH plays a role in the course of disease in a patient with chronic renal failure. Renal osteodystrophy (RO) is a complex skeletal disease comprising osteitis fibrosa cystica (caused by PTH excess), osteomalacia—unmineralized bone matrix (caused by vitamin D deficiency), extraskeletal calcification/ossification (caused by abnormal calcium and phosphorus metabolism), and adynamic bone disease (contributed to by PTH suppression). Chronic renal failure patients can develop RO. Failing kidneys increase serum phosphorus (hyperphosphoremia) and decrease 1,25-dihydroxyvitamin D (1,25-D) production by the kidney. The former results in secondary hyperparathyroidism from decreased gastrointestinal calcium absorption and osteitis fibrosa cystica from increased PTH in response to an increase in serum phosphorus. The later causes hypocalcemia and osteomalacia. With the onset of secondary hyperparathyroidism, the parathyroid gland becomes less responsive to its hormonal regulators because of decreased expression of its calcium and vitamin D receptors. Serum calcium drops. RO can lead to digital gangrene, bone pain, bone fractures, and muscle weakness.

Determining circulating biologically active PTH levels in humans has been challenging. One major problem is that PTH is found at low levels, normally 10 pg/mL to 65 pg/mL. Coupled with extremely low circulating levels is the problem of the heterogeneity of PTH and its many circulating fragments. In many cases, immunoassays have faced substantial and significant interference from circulating PTH fragments. For example, some commercially available PTH kits have almost 100% cross-reactivity with the non-(1–84) PTH fragment, (see the LePage article).

PTH immunoassays have varied over the years. One early approach is a double antibody precipitation immunoassay found in U.S. Pat. No. 4,369,138 to Arnold W. Lindall et alia. A first antibody has a high affinity for a (65–84) PTH fragment. A radioactive labeled (65–84) PTH peptide is added to the sample with the first antibody to compete for the endogenous unlabeled peptide. A second antibody is added which binds to any first antibody and radioactive labeled PTH fragment complex, thereby forming a precipitate. Both precipitate and supernatant can be measured for radioactive activity, and endogenous PTH levels can be calculated therefrom.

In an effort to overcome PTH fragment interference, immunoradiometric two-site assays for intact PTH (I-PTH) have been introduced, such as Allegro® Intact PTH assay by the Nichol's Institute of San Juan Capistrano, California. In one version, a capture antibody specifically binds to the C-terminal portion of hPTH while a labeled antibody specifically binds to the N-terminal portion of the captured hPTH. In another, two monoclonal antibodies were used, both of which attached to the N-terminal portion of hPTH. Unfortunately, these assays have problems in that they measure but do not discriminate between wPTH and non-whole PTH peptide fragments. This inability comes to the fore in hyperparathyroid patients and renal failure patients who have significant endogenous concentrations of large, non-whole PTH fragments.

Recently, researchers have made a specific binding assay directed to the large N-terminal PTH fragments. (See. Gao, Ping et alia "*Immunochemicalluminometric assay with two monoclonal antibodies against the N-terminal sequence of*

*human parathyroid hormone*", Clinica Chimica Acta 245 (1996) 39–59.) This immunochemiluminometric assay uses two monoclonal antibodies to detect N-terminal (1–34) PTH fragments but not mid-portion PTH fragments or C-terminal PTH fragments. A key factor in the design of these assays is to eliminate any reaction with C-terminal PTH fragments.

DISCLOSURE OF THE INVENTION

The present invention relates to novel methods and devices for differentiating in a patient parathyroid diseases, (such as primary hyperparathyroidism, secondary hyperparathyroidism, and stages thereof), from normal or non-disease states; for monitoring the function of parathyroid glands either during or after treatment, i.e., intraoperation and after operation parathyroid function monitoring as well as therapeutic treatment; and also for monitoring the effects of therapeutic treatments for parathyroid related bone diseases and hyperparathyroidism. One detects the level in the serum or blood of at least one of three different parameters, namely, whole or non-fragmented parathyroid hormone in a biological sample, a large non-whole parathyroid hormone peptide fragment that can function as a parathyroid hormone antagonist, or the combination of the two values. By comparing the two values or by examining independently one of the above three values, one can differentiate parathyroid and bone disease states, as well as differentiate such states from normal states, as the relationship between these values, as well as the values themselves, change significantly between a normal person and a patient with a parathyroid disease.

The present invention incorporates a discovery that a large, non-whole PTH peptide fragment, a peptide having an amino acid sequence from between (SEQ ID No.2 [$PTH_{3-84}$]) and (SEQ ID No. 3 [$PTH_{34-84}$]), functions in vivo as a wPTH antagonist or inhibitor (PIN), (see FIG. 12). In other words, the binding of wPTH to PTH receptors and the subsequent biological activity are affected by the presence of this PIN peptide fragment. The PTH receptors can be tied up with respect to PTH or PTH analogs in that the PTH binding site is blocked. The relationship between the concentrations of wPTH and PIN vary with PTH related disease states, and thus, are indicative of such states. Equally useful in view of the discovery of the antagonist nature of PIN, the present invention relates to novel methods and devices for monitoring parathyroid related bone diseases, and resultant bone loss or build-up. Increased amounts of PIN can inhibit the calcium releasing activity of PTH.

In making a measurement of wPTH, one does not want to detect PIN. The method for measuring the amount of wPTH in a sample such as serum, plasma, or blood comprises four general steps which can vary depending upon whether one uses a first antibody or antibody fragment specific for the PTH peptide SER-VAL-SER-GLU-ILE-GLN-LEU-MET (SEQ ID No.4), wherein at east four amino acids are part of the antibody reactive portion of the peptide either as a signal antibody or a capture antibody in conventional immunoassay formats. (One can also use an analogous peptide present in other species, such as a rat peptide in which the first amino acid serine is substituted with an alanine, SEQ ID No. 7.) Used either as a signal antibody or as a capture antibody, enough antibody is added to bind all wPTH present. Next, one allows the first antibody to bind to any wPTH present, thereby forming a perplex. A specific binding label comprised of a second antibody and a conventional immunoassy label such as chemiluminescent agents, colorimetric agents, energy transfer agents, enzymes, fluorescent agents, and radioisotopes, is used to label the complex, preferably at the C-terminal end of wPTH, and can be added either substantially simultaneously with the first antibody or subsequent thereto. Finally, one uses conventional techniques to measure the amount of labeled complex, and thereby calculate wPTH levels in the sample. If used as a signal antibody, then the first antibody still attaches at the N-terminal end, but the second antibody would serve as a capture antibody that attaches at the C-terminal end.

In making a measurement of PIN, one can either measure it directly, or indirectly. An indirect measurement can be made by first measuring wPTH and then measuring total PTH. Subtracting the wPTH value from the total PTH value, one derives the PIN value. (For the purposes of the present invention, "total PTH" refers to the sum of wPTH, the naturally occurring predominant PTH receptor binding agonist, and PIN, the naturally occurring predominant PTH receptor binding antagonist.) A total PTH assay detects both PIN and wPTH by detecting the N-terminal end of PTH not at SEQ ID No. 4, the very end of the N-terminal. By detecting between about amino acids 7 to 38 of PTH, the assay can detect both. A commercially available assay for total PTH is available from Scantibodies Laboratory, Inc. of Santee, Calif. A direct measurement of total PTH can be made by using an antibody or antibody fragment specific for a portion of the PTH peptide LEU-MET-HIS-ASN-LEU-GLY-LYS-HIS-LEU-ALA-SER-VAL -GLU-ARG-MET-GLN-TRP-LEU-ARG-LYS-LYS-LEU-GLN-ASP-VAL-HIS -ASN-PHE-VAL-ALA-LEU-GLY (SEQ ID No. 5), which comprises amino acids 7 to 38 of PTH, (preferably between amino acids 9 to 34), wherein at least four amino acids are part of the antibody reactive portion of the peptide. Such an antibody or antibody fragment can be used in conventional immunoassay formats either as a signal antibody or a capture antibody.

To differentiate between parathyroid disease states and the normal state or to monitor the effects of therapeutic treatment for parathyroid disease states, one can compare the relationship between the values of wPTH, PIN, or total PTH, (the combination of wPTH and PIN), in other words, the relationship between the values of PIN and total PTH, between PIN and whole PTH, or between whole PTH and total PTH. For example, one can use a proportion between wPTH and total PTH, between PIN and total PTH, or between PIN and wPTH. (Comparisons can even take the form of a neural network of all these factors.) Regardless of the comparative method chosen, these values change significantly between a normal person and a patient with a parathyroid disease and between various stages of parathyroid diseases.

Alternatively, one can either differentiate between parathyroid disease states and the normal state or monitor the effects of therapeutic treatment for parathyroid disease states by examining independently the value of either wPTH, PIN, or total PTH alone.

BEST MODES FOR CARRYING OUT THE INVENTION

Figure 1:
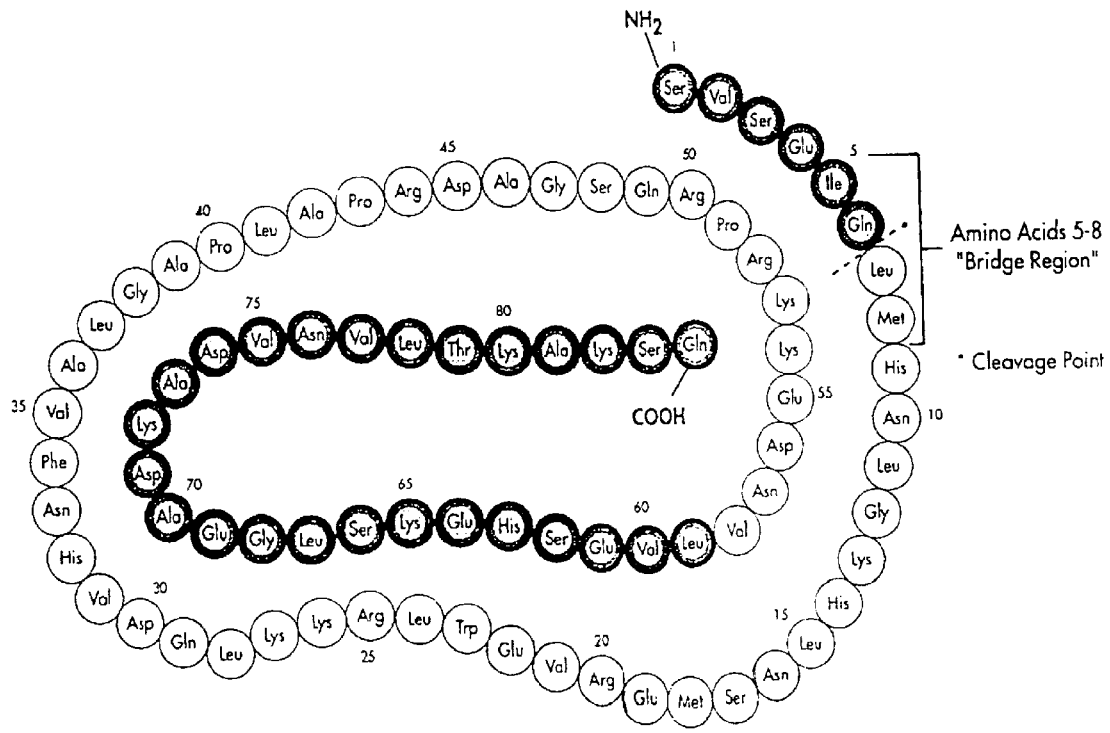
FIG. 1 is a diagrammatic view of human wPTH.

In disclosing the present invention, one should remember that there are a number of closely analogous, species dependent forms of PTH. The amino acid sequence of hPTH is shown in FIG. 1. However, for rat PTH, bovine PTH, or porcine PTH, for example, one finds the substitutions at some of the amino acids in the hPTH sequence. For the purposes of the present invention, one can use interchangeably antibodies or antibody fragments to forms of these PTHs, although it is preferred to use an antibody with specificity for PTH having a sequence matching the species in which the PTH measurements are made.

Whole PTH Immunoassay

Figure 2:
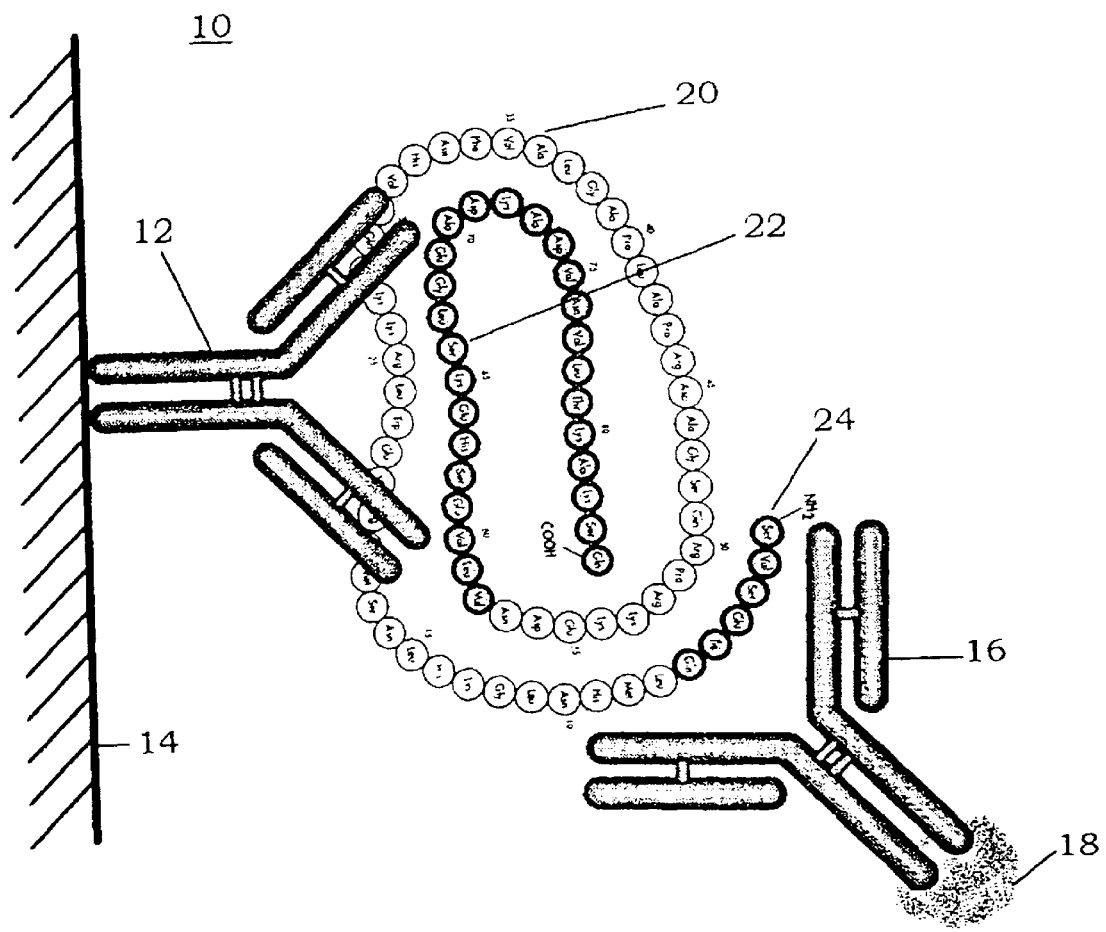
FIG. 2 is a diagrammatic view of a wPTH assay using the present antibody as a tracer element.
Figure 3:
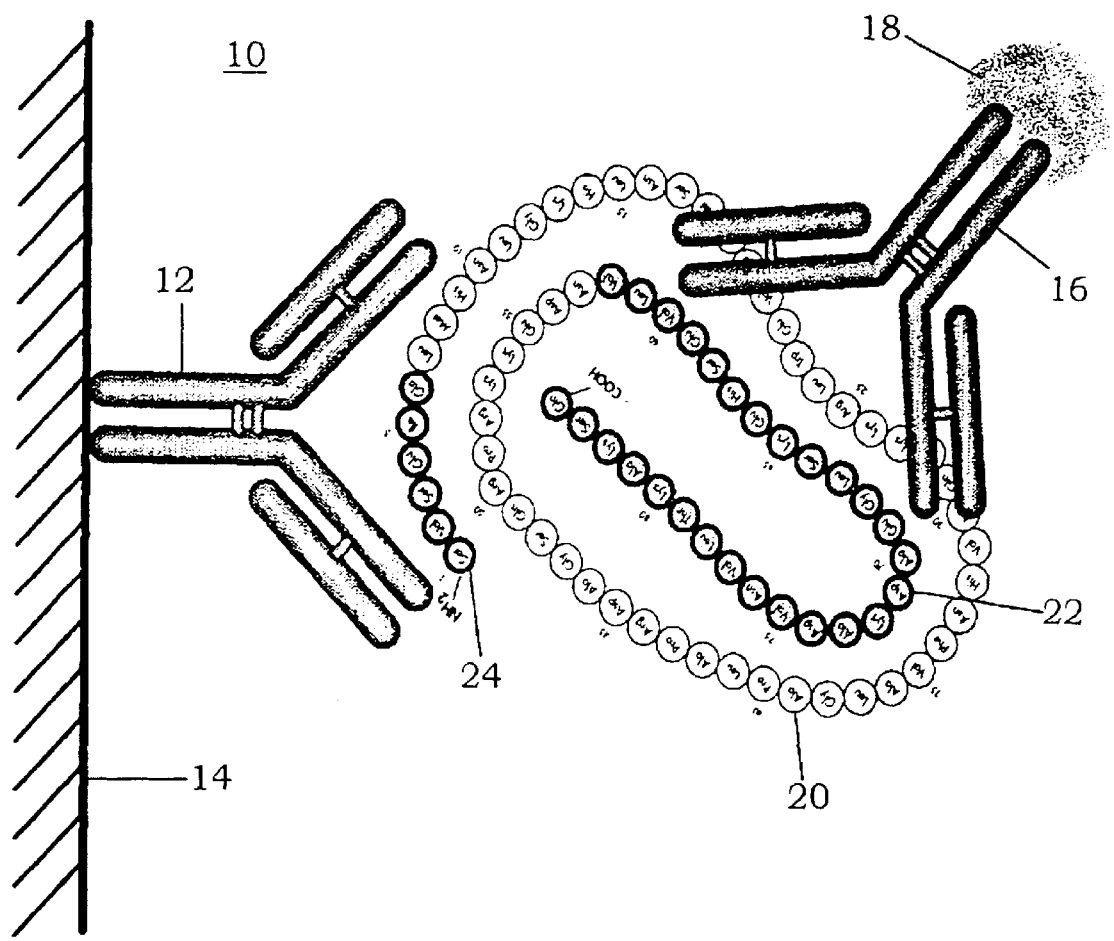
FIG. 3 is a diagrammatic view of a wPTH assay using the present antibody as a capture element.
Figure 4:
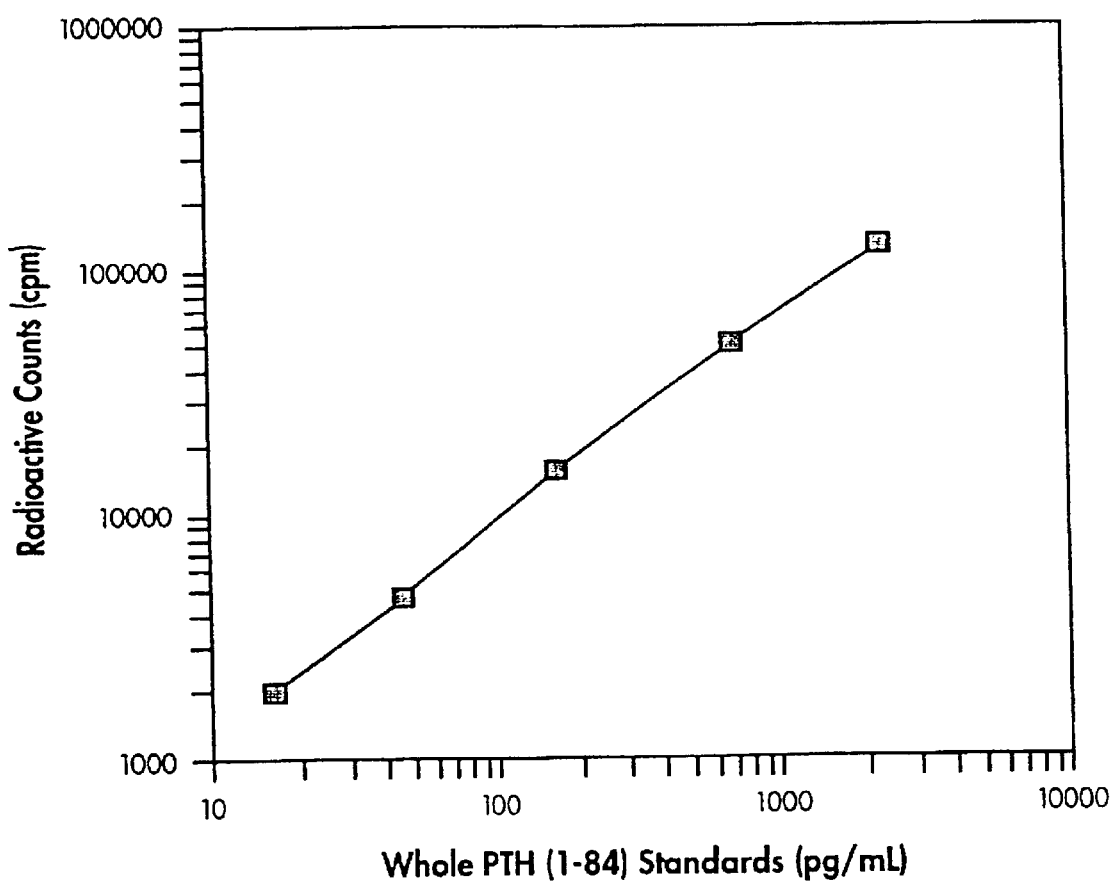
FIG. 4 is a graph showing a standard curve for a wPTH assay.

A preferred embodiment of the present invention is an immunoradiometric assay (IRMA), often referred to as a sandwich assay, as shown FIGS. 2 and 3. Elements employed in such an assay (10) include a capture antibody (12) attached to a solid support (14) and a signal antibody (16) having a label (18), attached thereto (20). Typically, one selects a capture antibody that is specific for C-terminal PTH fragments (22), while the label antibody is specific for the initial wPTH peptide sequence which comprises a domain for adenylate cyclase activation (24), as shown in FIG. 2. However, one could reverse the specificity of these antibodies, as is shown in FIG. 3.

Alternatively, one could create an immunoassay in which wPTH is either precipitated from solution or otherwise differentiated in a solution, as in conventional precipitating assays or turbidometric assays. For example, one can use at least three antibodies to form a precipitating mass. In addition to the initial wPTH sequence antibody and a C-terminal antibody, one can use at least a third antibody which attaches to the mid portion of PTH. The combined mass of wPTH and the at least three antibodies would form a labeled precipitating mass which can be measured by conventional techniques. Another method would be to couple the initial wPTH sequence antibody to colloidal solid supports, such as latex particles.

More specifically, one can create a signal antibody by iodinating 50 micrograms of affinity purified goat anti-(1–6) PTH antibody (Scantibodies Laboratory, Inc., Santee Calif., U.S.A.) by oxidation with chloramine T, incubation for 25 seconds at room temperature with 1 millicurie of 125-I radioisotope and reduction with sodium metabisulfate. Unincorporated 125-I radioisotope is separated from the 125-1-Goat anti-(1–6) PTH signal antibody by, passing the iodination mixture over a PD-10 desalting column (Pharmacia, Uppsala, Sweden) and following the manufacturers instructions. The fractions collected from the deserting column are measured in a gamma counter and those fractions representing the 125-1-goat anti-(1–6) PTH antibody are pooled and diluted to approximately 300,000 DPM (disintegrations per minute) per 100 microliters. This solution is the tracer solution to be used in the whole PTH IRMA.

Capture antibody coated tubes can be created by attaching affinity purified goat anti PTH 39–84 antibody, (Scantibodies Laboratory, Inc., Santee, Calif., U.S.A.), to 12 ×75 mm polystyrene tubes (Nunc, Denmark) by means of passive absorption techniques which are known to those of skill in the art. The tubes are emptied and dried, creating solid phase antibody coated tubes.

In order to make the signal antibody in the above assay, first one makes a synthetic PTH peptide corresponding either to hPTH (Ser-Val-Ser-Glu-lle-Gin-Leu-Met), SEQ ID No. 4, rat PTH (Ala-Val-Ser-Glu-lie Gln-Leu-Met), SEQ ID No. 7, or at least four amino acids in the common sequence. The selected peptide can play two roles in making an assay, first as a specific source for creating a polyclonal antibody or monoclonal antibody source for signal antibody or capture antibody, and second as part of an affinity purification means for isolating the desired signal antibody or capture antibody.

Initial Whole PTH Sequence Peptide

In order to make the signal antibody in the above assay, first one makes a synthetic PTH peptide corresponding either to hPTH (Ser-Val-Ser-GLU-ILE-Gln-Leu-Met), rat PTH (Ala-Val-Ser-Glu-Ile-Gln-Leu-Met), or at least four amino acids in the common sequence. The selected peptide can play two roles in making an assay, first as a specific source for creating a polyclonal antibody or monoclonal antibody source for signal antibody or capture antibody, and second as part of an affinity purification means for isolating the desired signal antibody or capture antibody.

Briefly, such a peptide can be synthesized on an Applied Biosystems, Inc. (Foster City, Calif., U.S.A.) Model 431 automated peptide synthesizer employing Fmoc (9-fluoronylmethoxycarbonyl) as the alpha-amino protecting group. All amino acids and solvents are from Applied Biosystems and are of synthesis grade. Following synthesis, the peptide is cleaved from the resin, and side chains are de-blocked, using a cleavage cocktail containing 6.67% phenol, 4.4% (v/v) thioanisole and 8.8% ethanedithiol in trifluoroacetic acid (TFA). The cleaved peptide is precipitated and washed several times in cold diethyl ether. It is then dissolved in water and lyophilized. The crude peptide is subjected to amino acid analysis (Waters PICO-TAG System, Boston, Mass., U.S.A.) and reversed-phase HPLC using a VYDAC (TM) C8 column with 0.1% TFA in water and 99.9% acetonitrile in 0.1% TFA as the mobile buffers. The presence of a single major peak along with the appropriate amino acid composition is taken as evidence that the peptide is suitable for further use.

The resulting peptide is then attached to cross linked agarose beads (activated Sepharose 4B from Pharmacia, Uppsala, Sweden) according to instructions from the manufacturer. Armed with the initial peptide sequence on a bead, one can affinity purify a polyclonal antibody serum source to isolate the initial sequence antibody for the wPTH immunoassay.

Initial Sequence Whole PTH Antibody

To create an affinity-purified anti-(1–6) PTH antibody, one first uses a selected initial PTH sequence peptide as described above as part of an immunogen for injection into a goat. The peptide can be used either by itself as an injectable immunogen, incorporated into a non PTH peptide having a molecular weight, typically, of between about 5,000 and 10,000,000, or as part of the wPTH complete sequence. The immunogen is mixed with an equal volume of Freunds complete adjuvant which is a mixture of light mineral oil, Arlacel detergent, and inactivated mycobacterium tuberculosis bacilli. The resulting mixture is homogenized to produce an aqueous/oil emulsion which is injected into the animal (typically a goat) for the primary immunization. The immunogen dose is approximately 50–400 micrograms. The goats are injected monthly with the same dose of immunogen complex except no mycobacterium tuberculosis bacilli is used in these subsequent injections. The goats are bled monthly, approximately three months after the 20 primary immunization. The serum (or antiserum) is derived from each bleeding by separating the red blood cells from the blood by centrilgation and removing the antiserum which is rich in (1–6) PTH antibodies.

To purify the antiserum for the desired (1–6) PTH antibody, one packs a separation column with the initial PTH sequence peptide bound beads described above, washes the column and equilibrates it with 0.01 M phosphate buffered saline (PBS). The antiserum is loaded onto the column and washed with 0.01 M PBS in order to remove antibodies without the (1–6) PTH specificity. The bound specific goat anti-(1–6) PTH polyclonal antibody is eluted from the solid phase PTH 1–6 in the column by passing an elution solution of 0.1 M glycine hydrochloride buffer, pH 2.5 through the column. The eluted polyclonal antibody is neutralized after it leaves the column with either the addition of 1.0 M phosphate buffer, pH 7.5 or by a buffer exchange with 0.01 M PBS, as is known to those of skill in the art. The polyclonal antibody is stored at 2–8 degrees centigrade.

Comparison Between Whole PTH and Total PTH Assays

Figure 10:
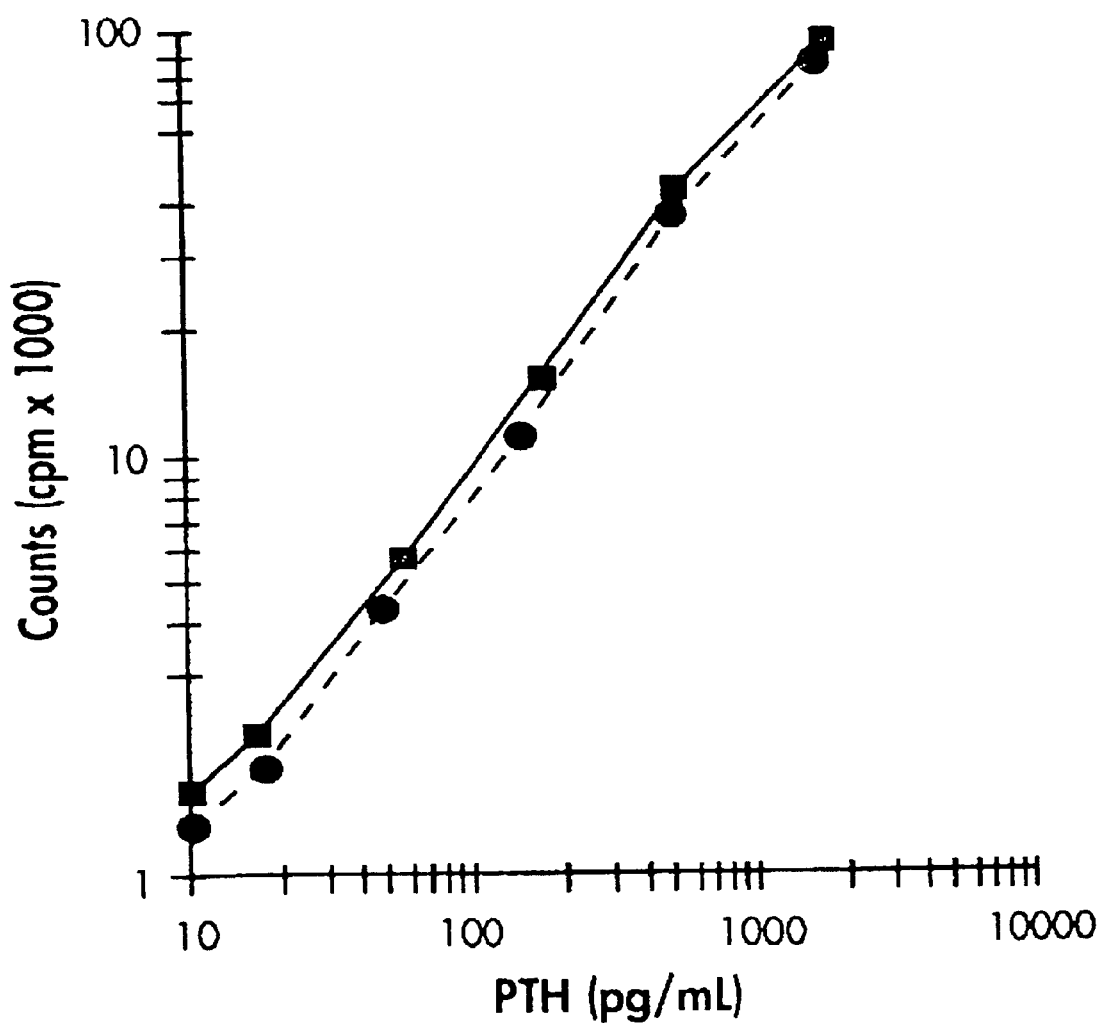
FIG. 10 is a graph demonstrating complete cross-reactivity of wPTH and PIN in a total PTH assay used in the present invention.
Figure 11:
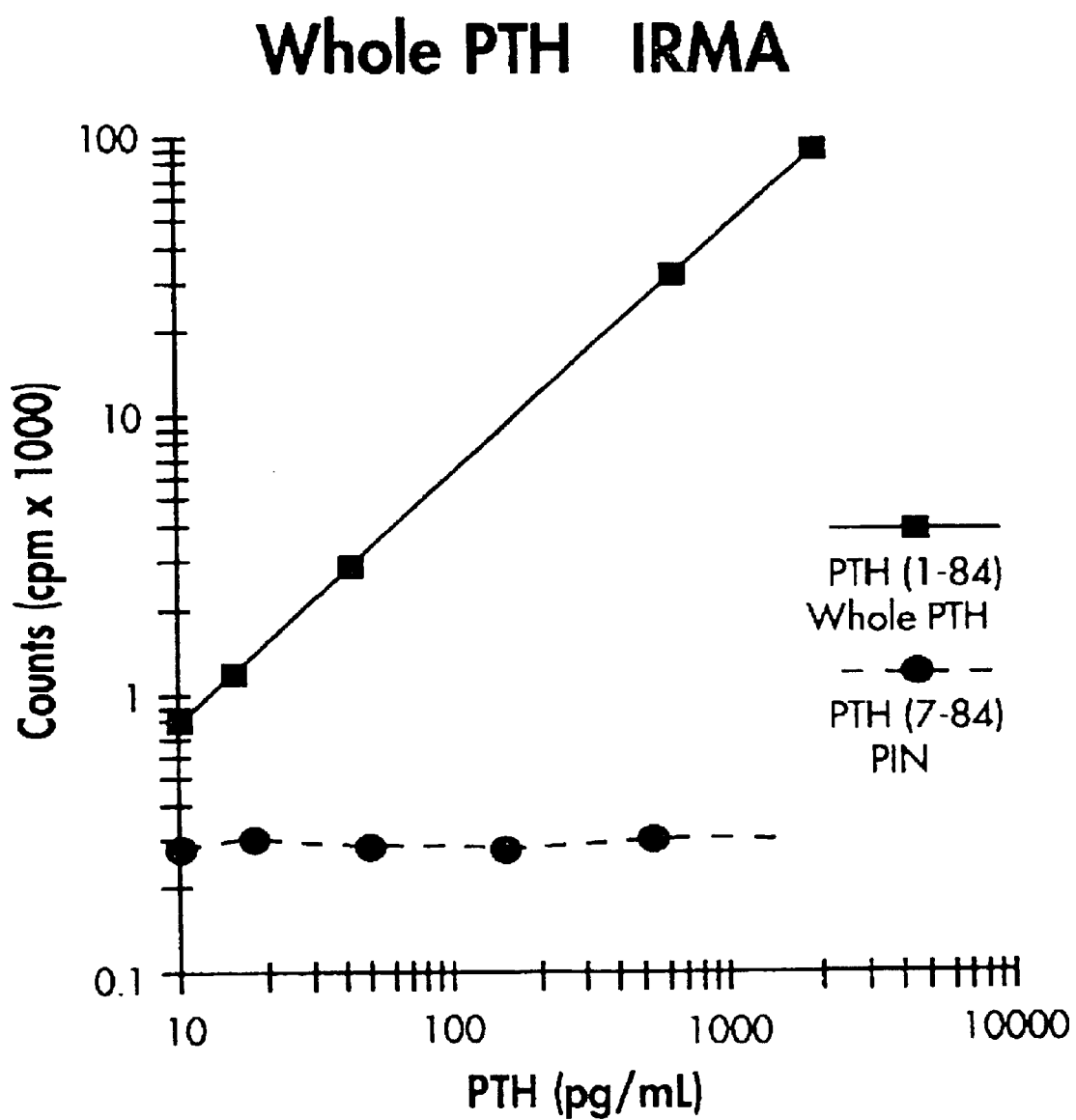
FIG. 11 is a graph demonstrating how the whole PTH assay used in the present invention does not detect to PIN.
Figure 12:
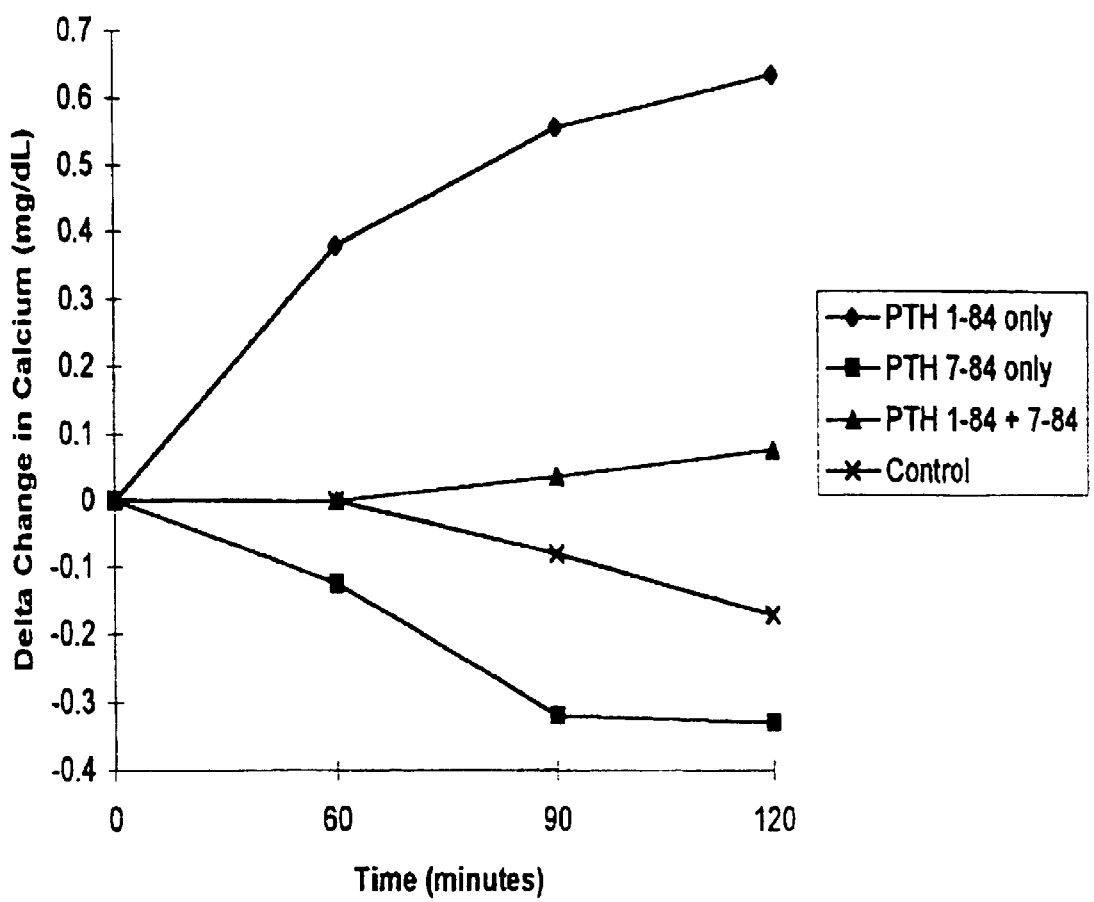
FIG. 12 is a graph demonstrating how PIN is an in vivo inhibitor of wPTH.

The present wPTH IRMA assay was compared to a conventional intact PTH or I-PTH immunoassay, the Allegro Nichols Intact-PTH assay, (which is commercially available and made by Nichols Institute Diagnostics of San Juan Capistrano, Calif., U.S.A.), in both PTH normal persons and those suffering from chronic uremia. This I-PTH immunoassay, due to its 100% cross reactivity between PIN and wPTH, is in actuality a total PTH assay, (see FIG. 10).

Figure 5:
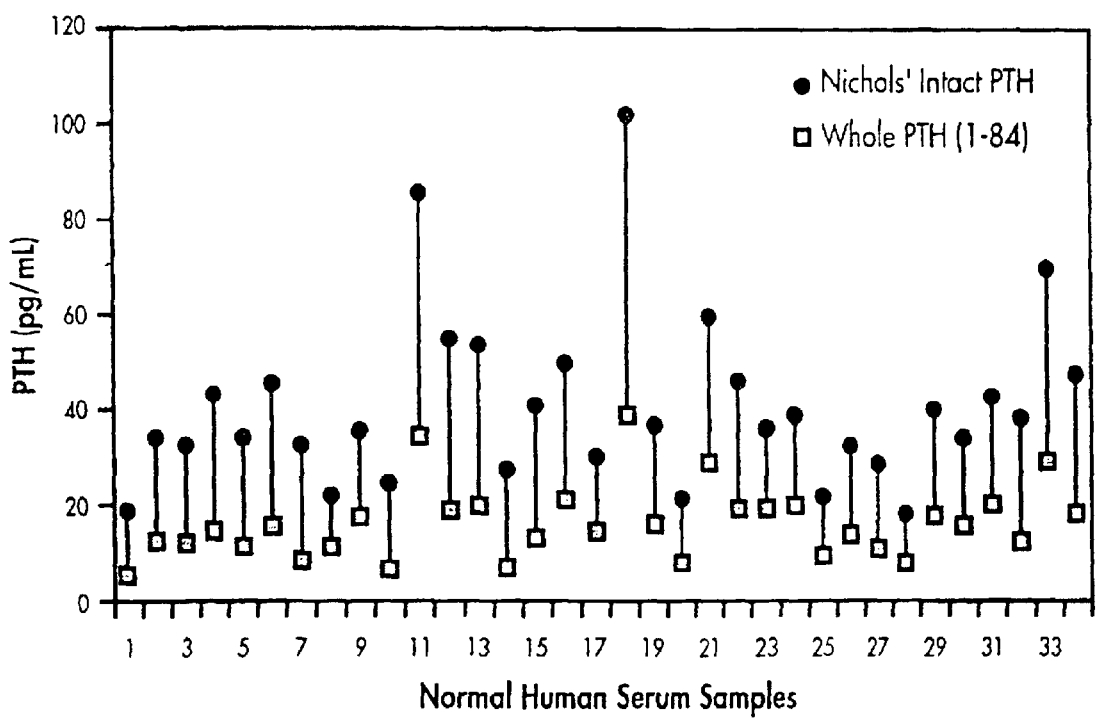
FIG. 5 is a graph comparing a conventional I-PTH assay with the present wPTH assay for healthy normal persons with "normal" PTH values.
Figure 6A:
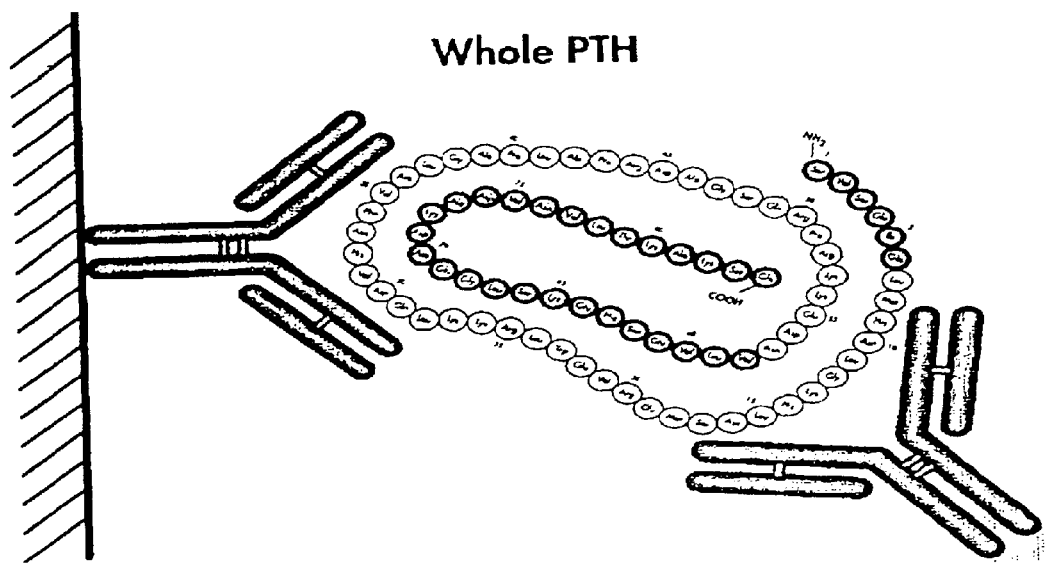
FIGS. 6A and 6B are diagrammatic views showing binding of whole (1–84)PTH compared with interference from non (1–84) PTH fragment (e.g., (7–94) PTH (SEQ ID NO:6)) in conventional I-PTH assays.
Figure 6B:
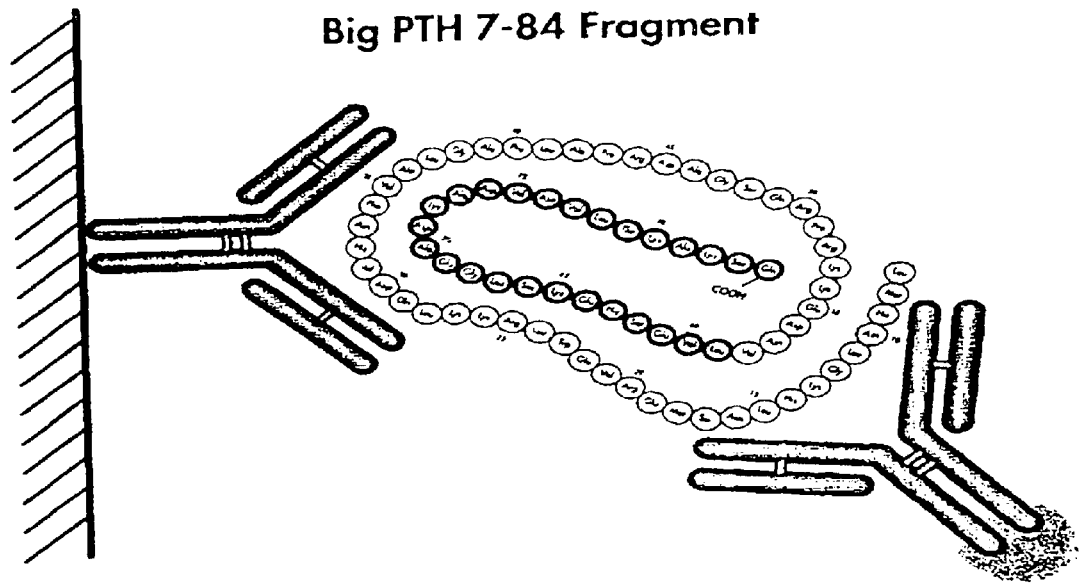

FIG. 5 shows the results for 34 normal human sewn samples from healthy subjects which were assayed both by the present wPTH IRMA and the above I-PTH assay. In every case, the level of wPTH detected by the IRMA is lower that reported by the I-PTH assay, demonstrating the ability of the present IRMA to avoid detecting the interfering large, non (1–81) PTH fragments detected by the I-PTH assay. FIGS. 6A and 6B illustrate how such interference can occur Au n-terminal PTH specific signal antibody which is not specific to the initial PTH peptide sequence, as in the present invention, can detect not only wPTH (as in FIG. 6A), but also can detect large, non (1–84) PTH fragments (as in FIG. 6B).

Figure 7:
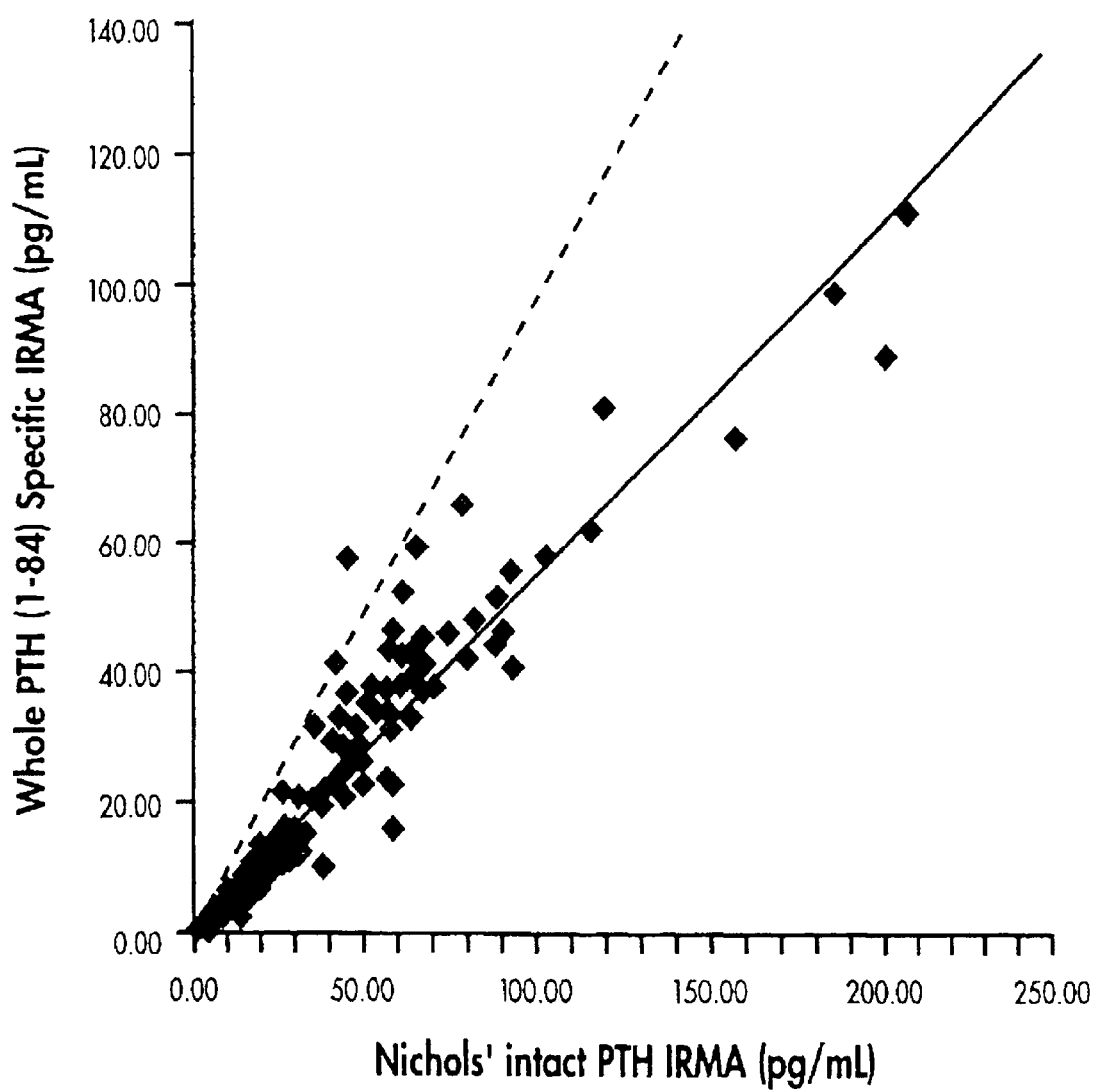
FIG. 7 is a graph comparing a conventional I-PTH assay with the present wPTH assay for patients with chronic uremia.
Figure 8:
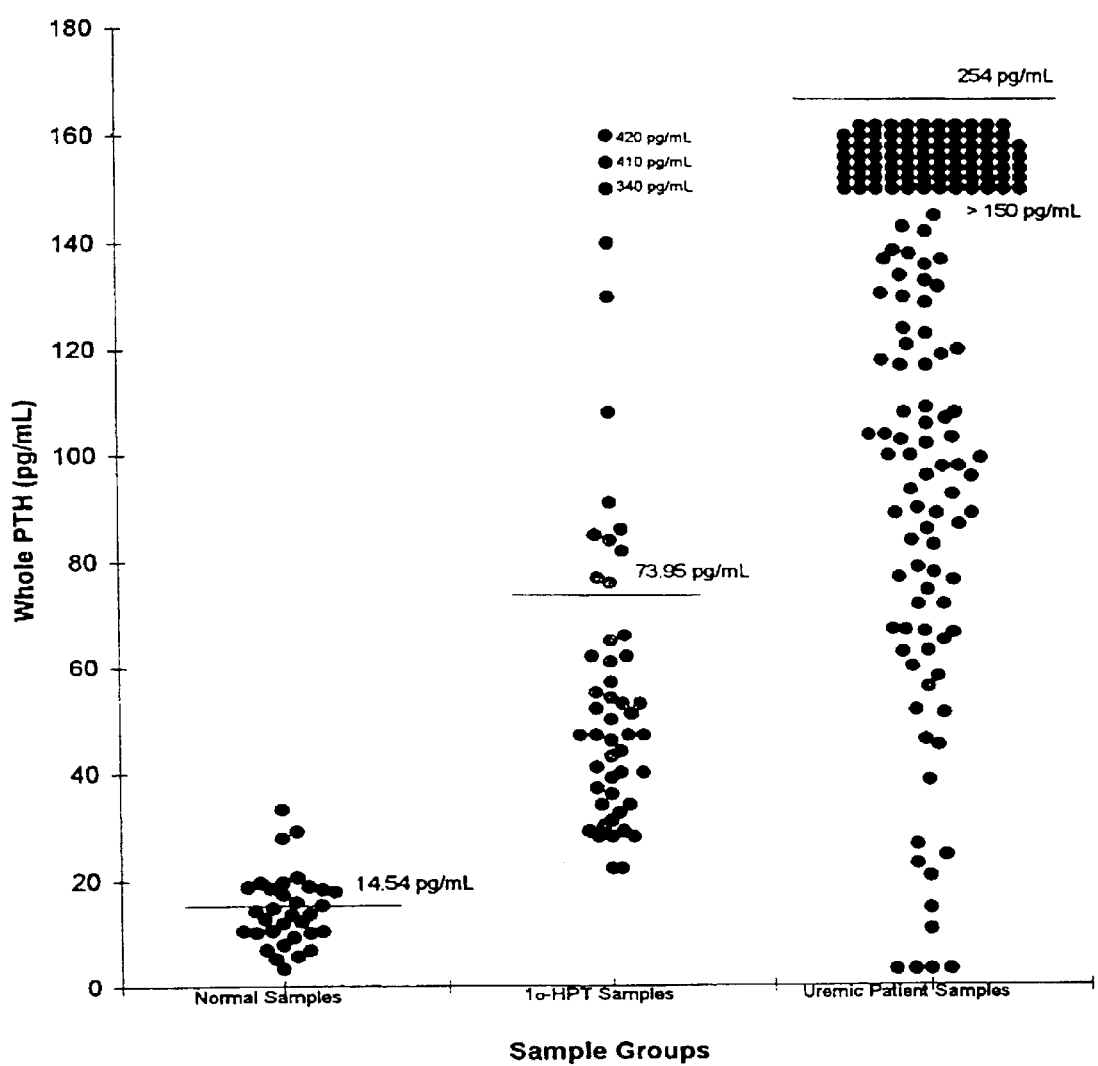
FIG. 8 is a graph showing the distribution of wPTH values for healthy normal persons, patients with primary hyperparathyroidism, and patients with chronic uremia.
Figure 9:
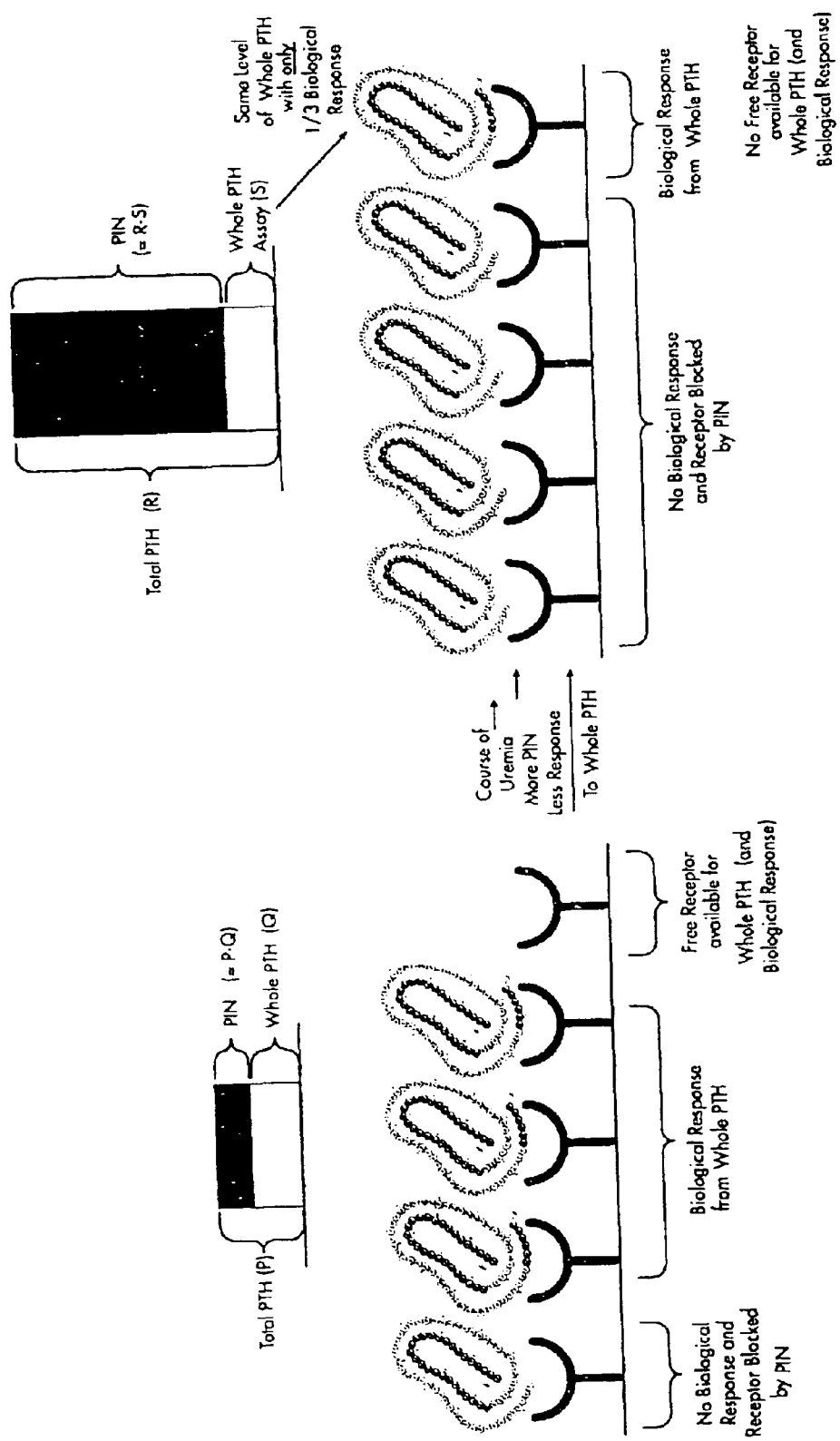
FIG. 9 is a diagrammatic view showing how PIN blocks the action of wPTH at the receptor level, thereby making the person insensitive to the biological effects of wPTH.

A comparison of assay results for 157 chronic uremic patients is shown in FIG. 7. Serum samples from these patients were measured using the wPTH IRMA and the above I-PTH assay. In every case the wPTH levels are lower than I-PTH values.

Clinical Use

The present wPTH and PIN assays have been used in a clinical setting involving 188 persons. The group included 31 persons having normal healthy parathyroid glands and 157 patients with chronic uremia who are undergoing dialysis on a continuous basis. Each person had a blood sample drawn which was assayed using a wPTH assay from Scantibodies Laboratory, Inc. as well as an I-PTH assay from Nichols Institute which gave total PTH values.

Table 1 shows the results individually and comparatively, of the wPTH, PIN, and total PTH assays from chronic uremic patients on dialysis.

TABLE 1

| Patient No. | Total PTH pg/ml | Whole PTH pg/ml | PIN pg/ml | PIN to Total PTH | PIN to Whole PTH | Whole PTH to Total PTH |
|---|---|---|---|---|---|---|
| 1 | 1410 | 740 | 670 | 48% | 91% | 52% |
| 2 | 185 | 89 | 96 | 52% | 108% | 48% |
| 3 | 231 | 104 | 127 | 55% | 122% | 45% |
| 4 | 1020 | 590 | 430 | 42% | 73% | 53% |
| 5 | 270 | 159 | 111 | 41% | 70% | 59% |
| 6 | 201 | 100 | 101 | 50% | 101% | 50% |
| 7 | 380 | 100 | 280 | 74% | 280% | 26% |
| 8 | 460 | 277 | 183 | 40% | 66% | 60% |
| 9 | 380 | 197 | 183 | 48% | 93% | 52% |
| 10 | 880 | 522 | 358 | 41% | 69% | 59% |
| 11 | 310 | 154 | 156 | 50% | 101% | 50% |
| 12 | 880 | 451 | 429 | 49% | 95% | 51% |
| 13 | 670 | 418 | 252 | 38% | 60% | 63% |
| 14 | 390 | 221 | 169 | 43% | 76% | 57% |
| 15 | 170 | 108 | 62 | 36% | 57% | 64% |
| 16 | 510 | 381 | 129 | 25% | 34% | 75% |
| 17 | 200 | 67 | 133 | 67% | 199% | 34% |
| 18 | 170 | 109 | 61 | 36% | 56% | 64% |
| 19 | 360 | 199 | 161 | 45% | 81% | 55% |
| 20 | 260 | 164 | 96 | 37% | 59% | 63% |
| 21 | 440 | 372 | 68 | 15% | 18% | 85% |
| 22 | 120 | 51.7 | 68.3 | 57% | 132% | 43% |
| 23 | 600 | 527 | 73 | 12% | 14% | 83% |
| 24 | 220 | 130 | 90 | 41% | 69% | 59% |
| 25 | 190 | 136 | 54 | 28% | 40% | 72% |
| 26 | 220 | 118 | 102 | 46% | 86% | 54% |
| 27 | 630 | 334 | 296 | 47% | 89% | 53% |
| 28 | 150 | 90 | 60 | 40% | 67% | 60% |
| 29 | 170 | 106 | 64 | 38% | 60% | 62% |
| 30 | 810 | 489 | 321 | 40% | 66% | 60% |
| 31 | 570 | 319 | 251 | 44% | 79% | 56% |
| 32 | 570 | 467 | 103 | 18% | 22% | 82% |
| 33 | 400 | 300 | 100 | 25% | 33% | 75% |
| 34 | 560 | 378 | 182 | 33% | 48% | 68% |

TABLE 1-continued

| Patient No. | Total PTH pg/ml | Whole PTH pg/ml | PIN pg/ml | PIN to Total PTH | PIN to Whole PTH | Whole PTH to Total PTH |
|---|---|---|---|---|---|---|
| 35 | 310 | 121 | 189 | 61% | 156% | 39% |
| 36 | 240 | 98 | 142 | 59% | 145% | 41% |
| 37 | 280 | 133 | 157 | 54% | 118% | 48% |
| 38 | 230 | 124 | 106 | 46% | 85% | 54% |
| 39 | 350 | 319 | 31 | 9% | 10% | 91% |
| 40 | 200 | 133 | 67 | 34% | 50% | 67% |
| 41 | 920 | 564 | 356 | 39% | 63% | 61% |
| 42 | 210 | 89 | 121 | 58% | 136% | 42% |
| 43 | 1990 | 904 | 1086 | 55% | 120% | 45% |
| 44 | 300 | 212 | 88 | 29% | 42% | 71% |
| 45 | 260 | 132 | 128 | 49% | 97% | 51% |
| 46 | 140 | 72 | 68 | 49% | 94% | 51% |
| 47 | 250 | 129 | 121 | 48% | 94% | 52% |
| 48 | 130 | 72 | 58 | 45% | 81% | 56% |
| 49 | 1840 | 1000 | 840 | 46% | 84% | 54% |
| 50 | 280 | 167 | 113 | 40% | 68% | 60% |
| 51 | 490 | 268 | 222 | 45% | 83% | 55% |
| 52 | 150 | 77.1 | 72.9 | 49% | 95% | 51% |
| 53 | 140 | 58.1 | 81.9 | 59% | 141% | 42% |
| 54 | 210 | 92.7 | 117.3 | 56% | 127% | 44% |
| 55 | 160 | 79 | 81 | 51% | 103% | 49% |
| 56 | 480 | 296 | 184 | 38% | 62% | 62% |
| 57 | 480 | 281 | 199 | 41% | 71% | 59% |
| 58 | 270 | 120 | 150 | 56% | 125% | 44% |
| 59 | 97 | 45 | 52 | 54% | 116% | 46% |
| 60 | 330 | 154 | 176 | 53% | 114% | 47% |
| 61 | 110 | 56 | 54 | 49% | 96% | 51% |
| 62 | 660 | 456 | 204 | 31% | 45% | 69% |
| 63 | 300 | 137 | 163 | 54% | 119% | 46% |
| 64 | 240 | 145 | 95 | 40% | 66% | 60% |
| 65 | 100 | 66.5 | 33.5 | 34% | 50% | 67% |
| 66 | 410 | 416.3 | −6.3 | −2% | −2% | 102% |
| 67 | 410 | 235.7 | 174.3 | 43% | 74% | 57% |
| 68 | 45 | 14.4 | 30.6 | 68% | 213% | 32% |
| 69 | 200 | 102.3 | 97.7 | 49% | 96% | 51% |
| 70 | 300 | 134 | 166 | 55% | 124% | 45% |
| 71 | 320 | 202 | 118 | 37% | 58% | 63% |
| 72 | 440 | 254 | 186 | 42% | 73% | 58% |
| 73 | 190 | 99.6 | 90.4 | 48% | 91% | 52% |
| 74 | 160 | 74.6 | 85.4 | 53% | 114% | 47% |
| 75 | 600 | 429.8 | 170.2 | 28% | 40% | 72% |
| 76 | 1140 | 632 | 508 | 45% | 80% | 55% |
| 77 | 440 | 211 | 229 | 52% | 109% | 48% |
| 78 | 450 | 276 | 174 | 39% | 63% | 61% |
| 79 | 510 | 344 | 166 | 33% | 48% | 67% |
| 80 | 190 | 62.8 | 127.2 | 67% | 203% | 33% |
| 81 | 170 | 86 | 84 | 49% | 98% | 51% |
| 82 | 180 | 103.4 | 76.6 | 43% | 74% | 57% |
| 83 | 78 | 22.7 | 55.3 | 71% | 244% | 29% |
| 84 | 230 | 117 | 113 | 49% | 97% | 51% |
| 85 | 160 | 96 | 64 | 40% | 67% | 60% |
| 86 | 220 | 89 | 131 | 60% | 147% | 40% |
| 87 | 470 | 321.5 | 148.5 | 32% | 46% | 68% |
| 88 | 310 | 137 | 173 | 56% | 126% | 44% |
| 89 | 2050 | 1127 | 923 | 45% | 82% | 55% |
| 90 | 930 | 414 | 516 | 55% | 125% | 45% |
| 91 | 180 | 65 | 115 | 64% | 177% | 36% |
| 92 | 560 | 238 | 322 | 58% | 135% | 43% |
| 93 | 640 | 597 | 43 | 7% | 7% | 93% |
| 94 | 590 | 382 | 208 | 35% | 54% | 65% |
| 95 | 270 | 103 | 167 | 62% | 162% | 38% |
| 96 | 560 | 349 | 211 | 38% | 60% | 62% |
| 97 | 180 | 78 | 102 | 57% | 131% | 43% |
| 98 | 790 | 429 | 361 | 46% | 84% | 54% |
| 99 | 670 | 372 | 298 | 44% | 80% | 56% |
| 100 | 140 | 20.4 | 119.6 | 85% | 586% | 15% |
| 101 | 190 | 117 | 73 | 38% | 62% | 62% |
| 102 | 190 | 108 | 82 | 43% | 76% | 57% |
| 103 | 430 | 217 | 213 | 50% | 98% | 50% |
| 104 | 560 | 439 | 121 | 22% | 28% | 78% |
| 105 | 500 | 357.7 | 142.3 | 28% | 40% | 72% |
| 106 | 1560 | 777 | 783 | 50% | 101% | 50% |
| 107 | 62 | 24.3 | 37.7 | 61% | 155% | 39% |
| 108 | 430 | 226 | 204 | 47% | 90% | 53% |
| 109 | 160 | 67.2 | 92.8 | 58% | 138% | 42% |
| 110 | 530 | 346 | 184 | 35% | 53% | 65% |
| 111 | 260 | 142 | 118 | 45% | 83% | 55% |
| 112 | 580 | 163 | 417 | 72% | 256% | 28% |
| 113 | 440 | 579 | −139 | −32% | −24% | 132% |
| 114 | 500 | 232.3 | 267.7 | 54% | 115% | 46% |
| 115 | 160 | 60 | 100 | 63% | 167% | 38% |
| 116 | 340 | 202 | 138 | 41% | 68% | 59% |
| 117 | 260 | 138 | 122 | 47% | 88% | 53% |
| 118 | 260 | 119 | 141 | 54% | 118% | 46% |
| 119 | 160 | 84 | 76 | 48% | 90% | 53% |
| 120 | 130 | 46 | 84 | 65% | 183% | 35% |
| 121 | 190 | 104 | 86 | 45% | 83% | 55% |
| 122 | 420 | 334 | 86 | 20% | 26% | 80% |
| 123 | 630 | 440 | 190 | 30% | 43% | 70% |
| 124 | 75 | 26.4 | 48.6 | 65% | 184% | 35% |
| 125 | 260 | 143 | 117 | 45% | 82% | 55% |
| 126 | 640 | 409 | 231 | 36% | 56% | 64% |
| 127 | 130 | 66.7 | 63.3 | 49% | 95% | 51% |
| 128 | 700 | 381 | 319 | 46% | 84% | 54% |
| 129 | 560 | 376 | 184 | 33% | 49% | 67% |
| 130 | 240 | 107 | 133 | 55% | 124% | 45% |
| 131 | 110 | 63 | 47 | 43% | 75% | 57% |
| 132 | 420 | 297 | 123 | 29% | 41% | 71% |
| 133 | 580 | 229 | 351 | 61% | 153% | 39% |
| 134 | 310 | 201.2 | 108.8 | 35% | 54% | 65% |
| 135 | 160 | 97.9 | 62.1 | 39% | 63% | 61% |
| 136 | 290 | 138.7 | 151.3 | 52% | 109% | 48% |
| 137 | 200 | 96.2 | 103.8 | 52% | 108% | 48% |
| 138 | 770 | 662.7 | 107.3 | 14% | 16% | 86% |
| 139 | 290 | 130.7 | 159.3 | 55% | 122% | 45% |
| 140 | 260 | 219 | 41 | 16% | 19% | 84% |
| 141 | 350 | 211 | 139 | 40% | 66% | 60% |
| 142 | 730 | 463.5 | 266.5 | 37% | 57% | 63% |
| 143 | 490 | 231 | 259 | 53% | 112% | 47% |
| 144 | 160 | 87 | 73 | 46% | 84% | 54% |
| 145 | 380 | 222 | 158 | 42% | 71% | 58% |
| 146 | 210 | 93.5 | 116.5 | 55% | 125% | 45% |
| 147 | 630 | 383.4 | 246.6 | 39% | 64% | 61% |
| 148 | 150 | 83.2 | 66.8 | 45% | 80% | 55% |
| 149 | 320 | 152.5 | 167.5 | 52% | 110% | 48% |
| 150 | 900 | 467.6 | 432.4 | 48% | 92% | 52% |
| 151 | 1180 | 818.6 | 361.4 | 31% | 44% | 69% |
| 152 | 120 | 38.4 | 81.6 | 68% | 213% | 32% |
| 153 | 5230 | 1388 | 3842 | 73% | 277% | 27% |
| 154 | 34 | 10.5 | 23.5 | 69% | 224% | 31% |
| 155 | 1020 | 590.6 | 429.4 | 42% | 73% | 58% |
| 156 | 180 | 76.6 | 103.4 | 57% | 135% | 43% |
| 157 | 120 | 51.1 | 68.9 | 57% | 135% | 43% |
| Median | 300 | 154 | 127 | 46% | 84% | 54% |

TABLE 2 shows the results, individually and comparatively, of the wPTH, PIN, and total PTH assays from the normals.

TABLE 2

| Patient No. | Total PTH pg/ml | Whole PTH pg/ml | PIN pg/ml | PIN to Total PTH | PIN to Whole PTH | Whole PTH to Total PTH |
|---|---|---|---|---|---|---|
| 1 | 17.13 | 3.32 | 13.81 | 81% | 416% | 19% |
| 2 | 32.92 | 10.49 | 22.43 | 68% | 214% | 32% |
| 3 | 31.32 | 10.31 | 21.01 | 67% | 204% | 33% |
| 4 | 41.84 | 12.72 | 29.12 | 70% | 229% | 30% |
| 5 | 33.03 | 10.09 | 22.94 | 69% | 227% | 31% |
| 6 | 44.32 | 14.23 | 30.09 | 68% | 211% | 32% |
| 7 | 31.47 | 6.8 | 24.67 | 78% | 363% | 22% |
| 8 | 20.82 | 10.03 | 10.79 | 52% | 108% | 48% |
| 9 | 34.64 | 15.95 | 18.69 | 54% | 117% | 46% |
| 10 | 23.69 | 5.25 | 18.44 | 78% | 351% | 22% |
| 11 | 53.98 | 17.82 | 36.16 | 67% | 203% | 33% |
| 12 | 52.71 | 18.83 | 33.88 | 64% | 180% | 36% |

TABLE 2-continued

| Patient No. | Total PTH pg/ml | Whole PTH pg/ml | PIN pg/ml | PIN to Total PTH | PIN to Whole PTH | Whole PTH to Total PTH |
|---|---|---|---|---|---|---|
| 13 | 26.92 | 5.63 | 21.29 | 79% | 378% | 21% |
| 14 | 39.93 | 11.86 | 28.07 | 70% | 237% | 30% |
| 15 | 48.84 | 20.47 | 28.37 | 58% | 139% | 42% |
| 16 | 29.56 | 13.68 | 15.88 | 54% | 116% | 46% |
| 17 | 36.19 | 14.69 | 21.5 | 59% | 146% | 41% |
| 18 | 20.96 | 6.99 | 13.97 | 67% | 200% | 33% |
| 19 | 59.29 | 27.89 | 31.4 | 53% | 113% | 47% |
| 20 | 45.57 | 18.23 | 27.34 | 60% | 150% | 40% |
| 21 | 35.64 | 18.72 | 16.92 | 47% | 90% | 53% |
| 22 | 38.53 | 19.56 | 18.97 | 49% | 97% | 51% |
| 23 | 21.71 | 9.34 | 12.37 | 57% | 132% | 43% |
| 24 | 32.42 | 13.51 | 18.91 | 58% | 140% | 42% |
| 25 | 28.5 | 10.41 | 18.09 | 63% | 174% | 37% |
| 26 | 18.17 | 7.8 | 10.37 | 57% | 133% | 43% |
| 27 | 39.96 | 17.29 | 22.67 | 57% | 131% | 43% |
| 28 | 34.08 | 15.24 | 18.84 | 55% | 124% | 45% |
| 29 | 42.95 | 19.59 | 23.36 | 54% | 119% | 46% |
| 30 | 38.4 | 12.16 | 26.24 | 68% | 216% | 32% |
| 31 | 47.57 | 18.45 | 29.12 | 61% | 158% | 39% |
| Median | 34.64 | 13.51 | 21.5 | 61% | 158% | 39% |

Clearly, the statistically significant differences in the medians of these two groups demonstrates that one can differentiate between the two by using these assays alone or by comparing their respective values.

TABLE 3

| Sample Type | Total PTH (pg/mL) | Whole PTH (pg/mL) | PIN (pg/mL) | PIN to Total PTH | PIN to Whole PTH | Whole PTH to Total PTH |
|---|---|---|---|---|---|---|
| Chronic Uremia (n = 157) Medians | 300 | 154 | 127 | 46% | 84% | 55% |
| Normal (n = 31) Medians | 34.64 | 13.51 | 21.5 | 61% | 158% | 37% |
| P-Value | <0.0001 | <0.0001 | <0.0001 | <0.0001 | <0.0001 | <0.0001 |

The ordinarily skilled artisan can appreciate that the present invention can incorporate any number of the preferred features described above.

All publications or unpublished patent applications mentioned herein are hereby incorporated by reference thereto.

Other embodiments of the present invention are not presented here which are obvious to those of ordinary skill in the art, now or during the term of any patent issuing from this patent specification, and thus, are within the spirit and scope of the present invention.

We claim:

1. A method for differentiating between a person having substantially normal parathyroid function and having hyperparathyroidism comprising:
   a) obtaining a sample from a person to be tested;
   b) determining whole parathyroid hormone level in said sample using an antibody or an antibody fragment that distinguishes whole parathyroid hormone from a parathyroid hormone inhibitory peptide fragment, said antibody or antibody fragment being specific for the parathyroid hormone peptide SER-VAL-SER-GLU-ILE-GLN-LEU-MET (SEQ ID No:4), wherein at least four amino acids in said peptide sequence are part of a reactive portion with said antibody, determining total parathyroid hormone level in said sample and determining parathyroid hormone inhibitory peptide fragment level by subtracting said whole parathyroid hormone level from said total parathyroid hormone level; and
   c) comparing at least two parameters selected from the group consisting of said whole parathyroid hormone level, parathyroid hormone inhibitory peptide fragment level, and total parathyroid hormone level,
   thereby determining whether said person has substantially normal parathyroid function or has hyperparathyroidism.

2. The method of claim 1, wherein the sample is selected from the group consisting of a serum, a plasma and a blood sample.

3. The method of claim 1, wherein the whole parathyroid hormone level is compared with the parathyroid hormone inhibitory peptide fragment level.

4. The method of claim 1, wherein the whole parathyroid hormone level is compared with the total parathyroid hormone level.

5. The method of claim 1, wherein the parathyroid hormone inhibitory peptide fragment level is compared with the total parathyroid hormone level.

6. The method of claim 1, wherein the comparison is in the form of a ratio or proportion.

7. The method of claim 1, wherein the antibody is a goat anti-(1–6) parathyroid hormone antibody.

8. The method of claim 7, wherein the whole parathyroid hormone level is compared with the parathyroid hormone inhibitory peptide fragment level.

9. The method of claim 1, wherein the parathyroid hormone inhibitory peptide fragment is a peptide having an amino acid sequence from between $PTH_{3-84}$ (SEQ ID NO:2) and $PTH_{34-84}$ (SEQ ID NO:3) and functions in vivo as a parathyroid hormone antagonist or inhibitor (PIN).

10. The method of claim 1, wherein the parathyroid hormone inhibitory peptide fragment is a peptide having an amino acid sequence of human $PTH_{7-84}$ (SEQ ID No:6).

11. The method of claim 1, wherein the hyperparathyroidism is primary hyperparathyroidism.

12. The method of claim 1, wherein the hyperparathyroidism is secondary hyperparathyroidism.

13. The method of claim 1, wherein the hyperparathyroidism is caused by chronic renal failure.

14. A method for monitoring parathyroid related bone disease and treatment comprising:
   a) obtaining a sample from a person to be monitored;
   b) determining whole parathyroid hormone level using an antibody or an antibody fragment that distinguishes whole parathyroid hormone from a parathyroid hormone inhibitory peptide fragment, said antibody or antibody fragment being specific for the parathyroid hormone peptide SER VAL-SER-GLU-ILE-GLN-LEU-MET (SEQ ID NO:4), wherein at least four amino acids in said peptide sequence are part of a reactive portion with said antibody, determining total parathyroid hormone level in said sample and determining parathyroid hormone inhibitory peptide fragment level by subtracting said whole parathyroid hormone level from said total parathyroid hormone level; and
   c) comparing at least two parameter selected from the group consisting of said whole parathyroid hormone level, parathyroid hormone inhibitory peptide fragment level, and total parathyroid hormone level,
   thereby monitoring parathyroid related bone disease and treatment in said person.

15. The method of claim 14, wherein the comparison is in the form of a ratio or proportion.

16. The method of claim 14, wherein the whole parathyroid hormone level is compared with the parathyroid hormone inhibitory peptide fragment level.

17. The method of claim 14, wherein the parathyroid related bone disease is renal osteodystrophy.

18. The method of claim 17, wherein the renal osteodystrophy is selected from the group consisting of osteitis fibrosa, cystica, osteomalacia, extraskeletal calcification/ossification and an adynamic low bone turnover disease.

19. The method of claim 17, wherein the whole parathyroid hormone level is compared with the parathyroid hormone inhibitory peptide fragment level to monitor renal osteodystrophy and its event.

20. A method for monitoring effects of therapeutic treatment for hyperparathroidiem comprising:
   a) obtaining a sample from a person to be monitored;

b) determining whole parathyroid hormone level using an antibody or an antibody fragment that distinguishes whole parathyroid hormone from a parathyroid hormone inhibitory peptide fragment, said antibody or antibody fragment being specific for the parathyroid hormone peptide SER-VAL-SER-GLU-ILE-GLN-LEU-MET (SEQ ID NO:4), wherein at least four amino acids in said peptide sequence are part of a reactive portion with said antibody, determine total parathyroid hormone level in said sample and determining parathyroid hormone inhibitory peptide fragment level by subtracting said whole parathyroid hormone level from said total parathyroid hormone level; and c) comparing at least two parathyroid selected from the group consisting of said whole parathyroid hormone level, parathyroid hormone inhibitory peptide fragment level, and total parathyroid hormone level, thereby monitoring effects of the therapeutic treatment for hyperparathyroidism in said person.

21. The method of claim 20, wherein the comparison is in the form of a ratio or proportion.

22. The method of claim 20, wherein the whole parathyroid hormone level is compared with the parathyroid hormone inhibitory peptide fragment level.

23. The method of claim 20, wherein the therapeutic treatment for hyperparathyroidism is vitamin D or vitamin D analogues treatment, calcium treatment, or parathyroidectomy.

24. The method of claim 23, wherein the whole parathyroid hormone level is compared with the parathyroid hormone inhibitory peptide fragment level to monitor the effects of vitamin D or vitamin D analogues treatment, calcium treatment, or parathyroidectemy.

25. The method of claim 23, wherein the hyperparathyroidism is selected from the group consisting of primary hyperparathyroidism, secondary hyperparathyroidism, renal bone disease, renal osteodystrophy, osteitis fibrosa, cystica, osteomalacia, extraskeletal calcification/ossification and an adynamic low bone turnover disease.

26. The method of claim 14, wherein the parathyroid hormone inhibitory peptide fragment is a peptide having an amino acid sequence of human $PTH_{7-84}$ (SEQ. ID. No. 6).

27. The method of claim 20, wherein the parathyroid hormone inhibitory peptide fragment is a peptide having an amino acid sequence of human $PTH_{7-84}$ (SEQ. ID. No. 6).

* * * * *

SEQUENCE LISTING

<160> NUMBER OF SEQ ID NOS: 7

<210> SEQ ID NO 1
<211> LENGTH: 84
<212> TYPE: PRT
<213> ORGANISM: human parathyroid hormone peptide fragment

<400> SEQUENCE: 1

Ser Val Ser Glu Ile Gln Leu Met His Asn Leu Gly Lys His Leu
1               5                   10                  15

Asn Ser Met Glu Arg Val Glu Trp Leu Arg Lys Lys Leu Gln Asp
                20                  25                  30

Val His Asn Phe Val Ala Leu Gly Ala Pro Leu Ala Pro Arg Asp
                35                  40                  45

Ala Gly Ser Gln Arg Pro Arg Lys Lys Glu Asp Asn Val Leu Val
                50                  55                  60

Glu Ser His Glu Lys Ser Leu Gly Glu Ala Asp Lys Ala Asp Val
                65                  70                  75

Asn Val Leu Thr Lys Ala Lys Ser Gln
                80

<210> SEQ ID NO 2
<211> LENGTH: 82
<212> TYPE: PRT
<213> ORGANISM: human parathyroid hormone peptide fragment

<400> SEQUENCE: 2

Ser Glu Ile Gln Leu Met His Asn Leu Gly Lys His Leu Asn Ser
1               5                   10                  15

Met Glu Arg Val Glu Trp Leu Arg Lys Lys Leu Gln Asp Val His
                20                  25                  30

-continued

```
Asn Phe Val Ala Leu Gly Ala Pro Leu Ala Pro Arg Asp Ala Gly
            35                  40                  45

Ser Gln Arg Pro Arg Lys Lys Glu Asp Asn Val Leu Val Glu Ser
            50                  55                  60

His Glu Lys Ser Leu Gly Glu Ala Asp Lys Ala Asp Val Asn Val
            65                  70                  75

Leu Thr Lys Ala Lys Ser Gln
            80

<210> SEQ ID NO 3
<211> LENGTH: 51
<212> TYPE: PRT
<213> ORGANISM: human parathyroid hormone peptide fragment

<400> SEQUENCE: 3

Phe Val Ala Leu Gly Ala Pro Leu Ala Pro Arg Asp Ala Gly Ser
1               5                  10                  15

Gln Arg Pro Arg Lys Lys Glu Asp Asn Val Leu Val Glu Ser His
            20                  25                  30

Glu Lys Ser Leu Gly Glu Ala Asp Lys Ala Asp Val Asn Val Leu
            35                  40                  45

Thr Lys Ala Lys Ser Gln
            50

<210> SEQ ID NO 4
<211> LENGTH: 8
<212> TYPE: PRT
<213> ORGANISM: human parathyroid hormone peptide fragment

<400> SEQUENCE: 4

Ser Val Ser Glu Ile Gln Leu Met
1               5

<210> SEQ ID NO 5
<211> LENGTH: 32
<212> TYPE: PRT
<213> ORGANISM: human parathyroid hormone peptide fragment

<400> SEQUENCE: 5

Leu Met His Asn Leu Gly Lys His Leu Asn Ser Met Glu Arg Val
1               5                  10                  15

Glu Trp Leu Arg Lys Lys Leu Gln Asp Val His Asn Phe Val Ala
            20                  25                  30

Leu Gly

<210> SEQ ID NO 6
<211> LENGTH: 78
<212> TYPE: PRT
<213> ORGANISM: human parathyroid hormone peptide fragment

<400> SEQUENCE: 6

Leu Met His Asn Leu Gly Lys His Leu Asn Ser Met Glu Arg Val
1               5                  10                  15

Glu Trp Leu Arg Lys Lys Leu Gln Asp Val His Asn Phe Val Ala
            20                  25                  30

Leu Gly Ala Pro Leu Ala Pro Arg Asp Ala Gly Ser Gln Arg Pro
            35                  40                  45

Arg Lys Lys Glu Asp Asn Val Leu Val Glu Ser His Glu Lys Ser
            50                  55                  60
```

```
                                      -continued

Leu Gly Glu Ala Asp Lys Ala Asp Val Asn Val Leu Thr Lys Ala
                 65                  70                  75

Lys Ser Gln

<210> SEQ ID NO 7
<211> LENGTH: 8
<212> TYPE: PRT
<213> ORGANISM: rat parathyroid hormone peptide fragment

<400> SEQUENCE: 7

Ala Val Ser Glu Ile Gln Leu Met
1               5
```